United States Patent [19]
Higson

[11] Patent Number: 6,083,366
[45] Date of Patent: Jul. 4, 2000

[54] SENSOR

[75] Inventor: Seamus Patrick John Higson, Sheffield, United Kingdom

[73] Assignee: The Manchester Metropolitan University, Manchester, United Kingdom

[21] Appl. No.: 08/945,049

[22] PCT Filed: Apr. 18, 1996

[86] PCT No.: PCT/GB96/00922

§ 371 Date: Oct. 17, 1997

§ 102(e) Date: Oct. 17, 1997

[87] PCT Pub. No.: WO96/33403

PCT Pub. Date: Oct. 24, 1996

[30] Foreign Application Priority Data

Apr. 19, 1995 [GB] United Kingdom .................... 9507991

[51] Int. Cl.[7] .................................................. G01N 27/26
[52] U.S. Cl. .......................... 204/403; 204/400; 427/2.13
[58] Field of Search .................................... 204/403, 400, 204/406; 435/817; 205/777.5, 775; 427/2.11, 2.12, 2.13, 58

[56] References Cited

U.S. PATENT DOCUMENTS

| | | | |
|---|---|---|---|
| 4,762,594 | 8/1988 | Guruswamy | 204/1 |
| 4,963,245 | 10/1990 | Weetall | 204/403 |
| 5,120,421 | 6/1992 | Glass et al. | 204/406 |
| 5,403,451 | 4/1995 | Riviello et al. | 205/777.5 |
| 5,635,054 | 6/1997 | Girault et al. | 205/775 |

FOREIGN PATENT DOCUMENTS 9108474  6/1991  WIPO .

OTHER PUBLICATIONS

Meyer et al. ("Two–Dimensional Imaging of o2, H2O2, and Glucose distributions by an Array of 400 individually Addressable Microelectrodes", Anal. Chem. 1995, 67, 1164–1170), Apr. 1, 1995.

Madigan et al. ("Preparation of microarray electrodes by sonochemical ablation of polymer films", J. Electrochem. Soc. (1994), 141(30, L23–L24), Month Unknown 1994.

*Primary Examiner*—T. Tung
*Assistant Examiner*—Alex Noguerola
*Attorney, Agent, or Firm*—Baker Botts L.L.P.

[57] ABSTRACT

There is disclosed a sensor for an analyte comprising a working electrode assembly, itself comprising a micro-electrode array in which each micro-electrode is coated with a layer of redox state dependent conducting organic polymer, a counter electrode; a conductive medium containment into which the electrodes are disposed and a material for analysis may be introduced; means for applying an alternating electric polarizing potential across the electrodes; and means for detecting a variation in a conductimetric property across the {working electrode→counter electrode} plane in the presence of the analyte.

13 Claims, 1 Drawing Sheet

SENSOR

This invention relates to sensors for analytes present in solution.

Conductimetric sensors based on redox state dependent conducting organic polymers such as polypyrrole, polyaniline and polyindole are well known. Such sensors commonly comprise a layer of the conducting organic polymer bridging two closely spaced electrodes, and commonly rely upon the detection of changes in the resistance or ac impedance of the polymer. This change in resistance is caused by the interaction between the analyte—which may be present in solution or in the gas phase—and the polymer. An important area of application lies in the incorporation of enzymes into the organic polymer to produce 'biosensors' capable of quantitative sensing of biologically significant analytes. Exposure of the enzyme to the analyte induces catalytic activity which in turn induces conductivity changes within the enzyme trapping polymer matrix. Although the precise nature of the conductivity changes are unclear—and may well differ with different combinations of polymer and enzyme—local $H^+$ concentration effects and, in the case of oxidases, ketones and aldehydes, $H^2O^2$ generation have been implicated. Broadly speaking, the conductivity of the polymer is perturbed by the redox behaviour of the enzyme on exposure to the analyte. Since enzyme-substrate interactions are typically very specific, the associated biosensor represents a highly selective method of analyte detection.

However, it is usually only possible to bridge the electrodes by electrochemical growth of organic polymer if the electrodes are rather closely spaced (typically <20 $\mu$m). This upper limit imposes restrictions on the magnitude of the measured signal and also requires precise electrode geometries which in turn requires technically demanding and expensive fabrication procedures such as screen printing or silicon chip fabrication techniques.

An appealing alternative which circumvents the problem of precise electrode alignment would involve measuring the impedance or admittance of a polymer bridging an analyte solution and a planar working electrode; in such an arrangement measurements would be made in the {working electrode→polymer→analyte solution→counter electrode} plane. Detection of the analyte would be accomplished by detecting changes in the impedance or admittance of the polymer induced by interaction between the polymer and the analyte. However, the linear mass transport regime operating in this arrangement would inevitably result in a detection signal of insufficient magnitude for useful measurement.

The present invention is based upon the concept of incorporating within the above described arrangement a working electrode assembly which comprises an array of conducting organic polymer coated micro-electrodes. Such an electrode results in radial transport of the analyte, rendering feasible the use of the arrangement as a sensor.

The present invention further provides examples of such arrays of micro-electrodes and methods of fabricating same.

International Publication WO 91/08474 describes a method for fabricating a microelectrode by photoablation. The microelectrode was used in an amperometric assay method for the detection of heavy metals.

According to one aspect of the invention there is provided a sensor for an analyte comprising a working electrode assembly itself comprising a micro-electrode array in which each micro-electrode is coated with a layer of redox state dependent conducting organic polymer; a counter electrode; a conductive medium containment into which the electrodes are disposed and a material for analysis may be introduced; means for applying an alternating electric polarising potential across the electrodes; and means for detecting a variation in a conductimetric property across the {working electrode→counter electrode} plane in the presence of the analyte.

The conductive medium containment may comprise a conducting solution.

The conductimetric property may be the impedance across the {working electrode→counter electrode} plane.

The variation in the conductimetric property may be detected as a function it of the applied frequency.

Alternatively, said variation may be detected at a single applied frequency.

The working electrode may be fabricated by coating a planar electrode with an insulating polymer, sonically ablating the insulating polymer coating to produce a plurality of micro-pores, and depositing conducting organic polymer into said micro-pores. The conducting organic polymer may be deposited electrochemically or by other means such as chemical vapour deposition, photopolymerisation techniques or other thin or thick film surface coating technologies.

An enzyme may be entrapped within the semiconducting organic polymer matrices. The semiconducting organic polymer may be polyaniline, polypyrrole. polyindole or equivalents thereof. The enzyme may be a redox enzyme such as glucose oxidase, alcohol oxidase and alcohol dehydrogenase. Further, the planar electrode may be a noble metal or a conducting material such as carbon and the insulating polymer may be polydiaminobenzenedihydrochloride, Teflon, PVC or polyethylvinylbenzene.

According to a second aspect of the invention there is provided a method of fabricating a working electrode assembly comprising coating a planar electrode with an insulating polymer, sonically ablating the insulating polymer coating to produce a plurality of micro-pores, and depositing redox state dependent conducting organic polymer into said microphores.

The organic polymer may be deposited electrochemically, by chemical vapour deposition, photopolymerisation techniques or other thin or thick film surface in coating technologies.

An enzyme may be entrapped within the organic polymer matrices.

Sensors and methods of fabricating working electrode assemblies in accordance with the invention will now be described with reference to the accompanying drawings in which:

BRIEF DESCRIPTION OF THE DRAWINGS

| Figure 1 | is a schematic illustration of the electrode arrangement: |
|---|---|
| Figure 2 | is a schematic illustration of the control arrangement: |
| Figure 3 | shows a possible equivalent circuit; and |
| Figure 4 | is a graph of typical log (impedance) vs log (frequency) profiles at different analyte concentrations. |

PREFERRED EMBODIMENTS

Figure 1:
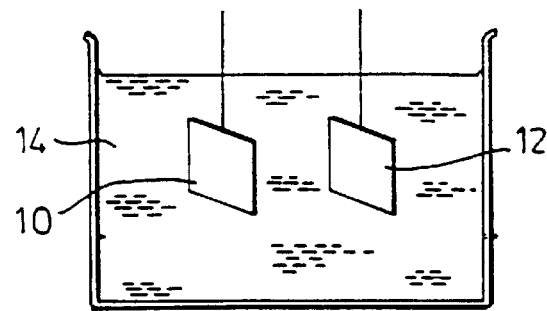
Figure 2:
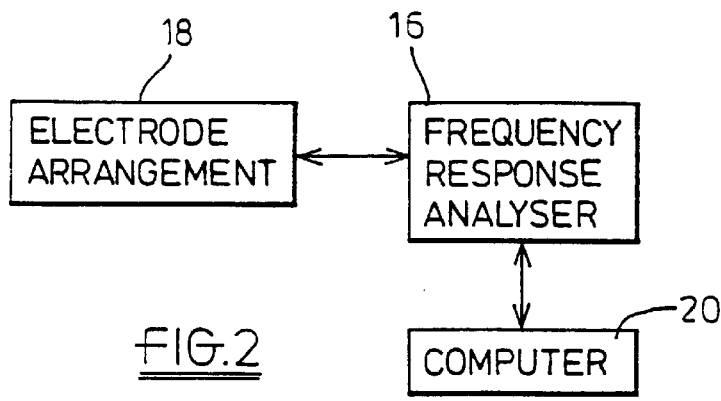

FIGS. 1 and 2 depict a sensor for detecting an analyte according to the present invention, which comprises a working electrode assembly 10, a counter electrode 12 and a conducting solution 14, wherein the working electrode assembly 10 comprises a micro-electrode array in which each micro-electrode is coated with a layer of redox state dependent conducting organic polymer. The sensor further comprises a frequency response analyser 16 which i) applies an alternating electric polarising potential across the electrode arrangement 18 and ii) detects any variation in a chosen conductimetric property across the {working electrode substrate→polymer→solution→counter electrode} plane when the analyte is present in the solution. The variation may alternatively be detected by a phase sensitive detector. Control of the frequency response analyser and collection of data may be effected inter alia by a computer 20 via a suitable interface.

The conductimetric sensor of the present invention utilises redox state dependent conducting organic polymer as the active, analyte sensing medium, but represents a very different detection arrangement to prior art conductimetric devices which employ polymers of this type. In particular, prior art devices typically comprise closely spaced electrodes bridged by conducting organic polymer, close in this context being about 15–20 $\mu$m or less. This approximate upper limit is due to difficulty of effectively bridging greater electrode separations with electrochemically grown polymer—by far the most commonly employed method of depositing the conducting polymer. Physically, the reason for this difficulty is that the separation of the electrodes exceeds the length of the polymeric chains, resulting in very high resistances and poor mechanical qualities. Consequently, precise electrode geometries are required necessitating the use of technically demanding and expensive fabrication procedures such as screen printing or silicon chip fabrication techniques.

The arrangement of the present invention does not utilise conducting polymer as an electrode bridge, and thus does not require precise alignment of the electrodes. Furthermore, it is noted that use of a conventional planar working electrode coated with semiconducting organic polymer would result in linear mass transport of the analyte, which in turn would result in an unfeasibly small detection signal. With the introduction of micro-electrodes the mass transport of analyte becomes radial in nature, permitting analyte detection with excellent sensitivity.

Figure 3:
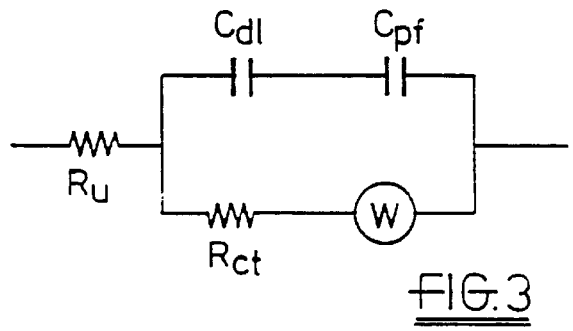

Detection of analyte may be achieved by detecting changes in the complex plane impedance between the counter electrode and the array of polymer coated micro-electrodes which comprise the working electrode. However, detection of other conductimetric properties, such as conductance or susceptance, are also within the scope of the invention. In any event, it is necessary to separate the desired measurement of analyte induced changes in, for example, polymer resistance from the other conductimetric components of the system. FIG. 3 shows a Randles equivalent circuit, which indicates that the conductimetric behaviour between the counter electrode and the working electrode may be decomposed into:

| | | |
|---|---|---|
| i) | | the uncompensated solution resistance $R_u$, |
| ii) | | the capacitance due to the electrical double layer $C_{dl}$, |
| iii) | | the reaction resistance, which may in turn comprise a Warburg impedance W and a charge transfer resistance $R_{ct}$, |
| iv) | | the capacitance of the polymer layer $C_{pf}$. |

The Warburg impedance W is negligible at high excitation frequencies (typically >100 Hz) and thus $R^{ct}$ and $C^{pf}$, which are modulated by the analyte-polymer interaction, may be extracted.

Figure 4:
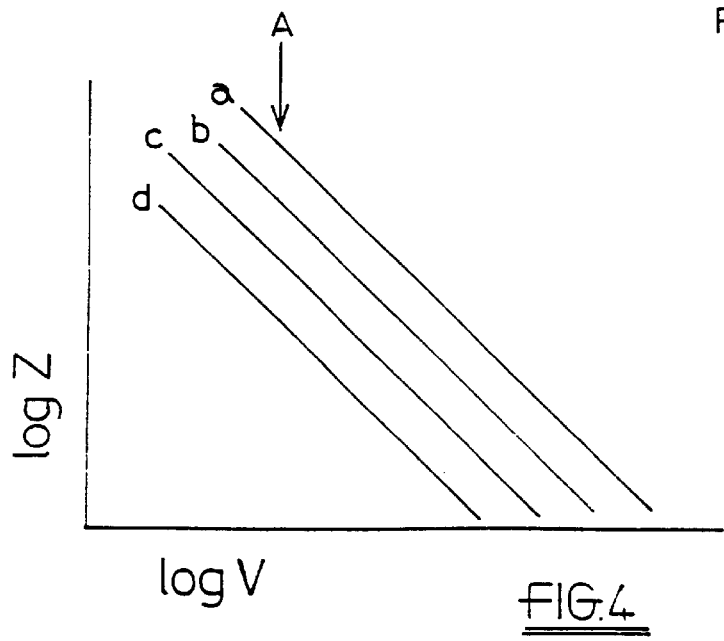

A schematic illustration of the way in which impedance may vary as a function of applied frequency and analyte concentration is shown in FIG. 4. The response curves a, b, c, d are in order of increasing analyte concentration. The presence of analyte may be detected by monitoring changes in the response function over a range of applied frequencies. Alternatively, it may prove expedient to detect changes in impedance at a fixed frequency, this frequency advantageously being one at which particularly large impedance changes are induced by the analyte-polymer combination in question, such as the frequency marked A in FIG. 4. The computer 20 may be used to store the response or response function obtained with no analyte present in the solution 14 as a reference signal, and to compare this reference signal with the response or response function obtained in the presence of an analyte.

Fourier transform analysis techniques are also applicable. However, it should be noted that a dc measurement of bulk sensor resistance would not suffice, since the dominant contribution to this resistance would be due to charging of the capacitances within the circuit, giving rise to a drifting value.

The invention also provides examples of arrays of semiconducting organic polymer coated micro-electrodes and methods of fabricating same. Generally speaking, working electrodes of the present invention may be fabricated by coating a planar electrode with an insulating polymer, sonically ablating the insulating polymer coating to produce a plurality of micro-pores, and depositing conducting organic polymer into the micro-pores. such that an electrically parallel connected micro-electrode array is formed. It has been shown (N A Madigan, C R S Hagan and L A Coury, J. Electrochem. Soc., 141 (1994) 1014) that micro-electrode arrays may be produced by sonicating insulating polymer coated electrodes, but the coating of the micro-electrodes with conducting organic polymer and the use of such a micro-electrode array as a sensor has no antecedent. Examples of insulating polymer films include polydiaminobenzenedihydrochloride, PVC, Teflon, polyethylvinylbenzene and the like. Examples of substrate electrode materials include gold, platinum, ruthenium, gold/platinum alloys and glassy carbon. Commonly employed solvents such as water, decane and dioxane may be used for sonication.

The conducting organic polymer may be deposited electrochemically, the precise details of the polymerisation process not varying substantially from well known literature methods. (see for example J C Cooper and E A H Hall. Biosensors & Bioelectronics, 7 (1992) 473) Examples of electropolymerisable conducting organic polymers include polyaniline, polypyrrole, polyindole and poly-N-methylpyrrole, although it is to be understood that this list is a non-limiting one: many examples of suitable conducting organic polymers may be found in the literature. Other deposition means, such as chemical vapour deposition, photopolymerisation techniques or other thin or thick film surface coating technologies are within the scope of the invention.

An important aspect of the present invention lies in the incorporation of enzymes into the conducting organic polymer to produce biosensors capable of sensing of, for example, biologically significant analytes. The incorporation of enzymes into the polymer may be accomplished by any of the many well characterised methods documented in the literature. For example, the polymer may be electrochemically polymerised from a solution containing both monomer and enzyme.

A specific example of a sensor of the present invention is a device sensitive to the presence of glucose. The working electrode was produced by sonication in water of a gold planar electrode coated with polydiaminobenzenedihydrochloride, followed by electropolymerisation of aniline in the presence of glucose oxidase. Sonication is typically at 15 KHz for one minute. Glucose oxidase catalyses the oxidation of glucose, i.e:

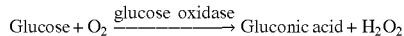

$$\text{Glucose} + O_2 \xrightarrow{\text{glucose oxidase}} \text{Gluconic acid} + H_2O_2$$

The choice of polyaniline as the conducting organic polymer is influenced by its stability in the presence of hydrogen peroxide. However, it should be noted that the use of other conducting organic polymers and other enzymes is within the scope of the invention. Measurements of impedance profile as a function of applied frequency at varying concentrations of the glucose analyte (1–20 mM glucose in a pH 7 phosphate buffer) have been made using a glucose sensor of this type. The results indicate that change in an impedance value measured at a chosen frequency (compared to the impedance obtained at the same frequency with no glucose present) is proportional to the concentration of glucose in the solution in the low (<5 mM) concentration regime. As an example, measurements made at a frequency of 11.3 Hz show that the impedance of the polymer film is ca. 400 Ω in the absence of glucose, but in the presence of a 5 mM glucose solution this impedance drops to ca. 200 Ω. This represents an extremely large signal, well above the detection limit of the apparatus employed, which is capable of detecting changes in resistance of the order of 0.1 Ω or less.

Similar results have been obtained with a sensor incorporating alcohol oxidase as the enzyme; ethanol is the analyte in this instance. This demonstrates that the present invention may be applied to different analyte and enzyme combinations. For ethanol concentrations of 15 mM, a drop in impedance from ca. 400 Ω to ca. 200 Ω has been observed.

Many further variations within the scope and spirit of the invention are possible. For instance, it may be desirable to combine several working electrodes within one device, wherein each working electrode comprises a different polymer and/or enzyme. In one example each working electrode would have a different enzyme incorporated into the polymer matrix, and each enzyme would be sensitive to a different analye. The resulting device would be sensitive to the presence of a number of specific analytes. Alternatively, it is well known that semiconducting organic polymer based conductimetric sensors which do not incorporate analyte reception agents such as enzymes are usually sensitive to a range of analytes. Therefore, with prior art devices which rely upon the measurement of changes in dc resistance, precise identification of an analyte with a single sensor incorporating a single polymer can present a problem. The present invention is advantageous in this respect, since the response of the sensor as a function of frequency can provide an extra detection dimensionality compared to a single, bulk, dc resistance measurement, and may be considered a 'fingerprint' of the analyte detected. However, it may be desirable to produce a device having a plurality of working electrodes which each involve a different semiconducting organic polymer; in such a device the pattern of response across the plurality of working electrodes may be indicative of a particular analyte. Indeed, it may prove possible to deduce the individual components of a mixture from the response patterns of such a device.

What is claimed is:

1. A sensor for an analyte comprising:

a working electrode comprising a conductive electrode having an insulating layer thereon, said insulating layer having a plurality of micropores therethrough, and a conducting organic polymer deposited in said micropores, said polymer in said micropores being electrically interconnected by said conductive electrode to form a microelectrode array;

a counter electrode;

a conductive medium containment into which the electrodes are disposed and a material for analysis may be introduced;

means for applying an alternating electric polarizing potential across the electrodes; and means for detecting a variation in a conductimetric property across a working electrode-counterelectrode plane in the presence of the analyte.

2. A sensor according to claim 1 in which the conductive medium containment comprises a conducting solution.

3. A sensor according to claim 1 or claim 2 in which the conductimetric property detected is the impedance across the {working electrode→counter electrode} plane.

4. A sensor according claim 1 in which the variation in the conductimetric property is detected as a function of the applied frequency.

5. A sensor according to claim 1 in which the variation in the conductimetric property is detected at a single applied frequency.

6. A sensor according claim 1 in which the working electrode is fabricated by coating a planar electrode with an insulating polymer, sonically ablating the insulating polymer coating to produce a plurality of micro-pores, and depositing redox state dependent organic polymer into said micro-pores.

7. A sensor according to claim 6 in which the conducting organic polymer is deposited electrochemically, by chemical vapour deposition or by photopolymerization.

8. A sensor according claim 6 in which an enzyme is entrapped within the conducting organic polymer matrices.

9. A sensor according to claim 8 in which the enzyme is glucose oxidase, alcohol oxidase or alcohol dehydrogenase.

10. A sensor according to any of claims 6 to 9 in which the insulating polymer is polydiaminobenzenedihydrochloride, Teflon, PVC or polyethylvinylbenzene.

11. A method of fabricating a working electrode assembly comprising coating a planar electrode with an insulating polymer, sonically ablating the insulating polymer coating to produce a plurality of micro-pores, and depositing redox state dependent conducting organic polymer into said micro-pores.

12. A method according to claim 11 in which the organic polymer is deposited electrochemically, by chemical vapour deposition or by photopolymerization.

13. A method according to claim 11 or claim 12 in which an enzyme is entrapped within the organic polymer matrices.

* * * * *

UNITED STATES PATENT AND TRADEMARK OFFICE
CERTIFICATE OF CORRECTION

PATENT NO. : 6,083,366
DATED : July 4, 2000
INVENTOR(S) : Higson

It is certified that error appears in the above-identified patent and that said Letters Patent is hereby corrected as shown below:

Column 6,
Line 28, "claim 1" should read -- to claim 1 --
Line 31, "claim 1" should read -- to claim 1 --
Line 34, "claim 1" should read -- to claim 1 --
Line 43, "claim 6" should read -- to claim 6 --

Column 2,
Line 50, "BRIEF DESCRIPTION OF THE DRAWINGS" should be moved to col. 2, line 46
Lines 53-59, description of drawings should be in regular text format- not table Column 3,
Lines 55-60, text should be in regular format-not table Signed and Sealed this Twenty-third Day of October, 2001

Attest:

NICHOLAS P. GODICI
Attesting Officer   Acting Director of the United States Patent and Trademark Office